(12) United States Patent
Kokish

(10) Patent No.: US 6,391,002 B1
(45) Date of Patent: May 21, 2002

(54) BALLOON WITH THE VARIABLE RADIAL FORCE DISTRIBUTION

(75) Inventor: Arkady Kokish, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/457,124

(22) Filed: Dec. 7, 1999

(51) Int. Cl.[7] .............................................. A61M 29/00
(52) U.S. Cl. ................................ 604/96.01; 604/103.06
(58) Field of Search ................ 604/96, 101, 916–921; 606/192–194

(56) References Cited

U.S. PATENT DOCUMENTS 5,314,443 A * 5/1994 Rudick ........................ 606/192
5,967,968 A * 10/1999 Briacoe et al. ............. 600/458
6,022,370 A * 2/2000 Tower ......................... 606/194
6,221,042 B1 4/2001 Adams ..................... 604/96.01

* cited by examiner

*Primary Examiner*—Manual Mendez
(74) *Attorney, Agent, or Firm*—Coudert Brothers LLP

(57) ABSTRACT

A balloon catheter having an elongated shaft and a balloon mounted on the distal portion of the shaft, the balloon having a working section and proximal and distal end portions that extend inwardly with respect to the working section and which are secured to the catheter shaft within the working section. The end portions are therefore inverted recesses on each end of the balloon. A stent may be disposed about the balloon to form a stent deploying system. The proximal and distal end portions may contain a tapered portion, which tapers from the balloon working section to the catheter shaft with decreasing transverse dimension. The end portions may be connected to the working section with connecting fibers. This design allows for improved expansion and stent placement in the vasculature.

23 Claims, 2 Drawing Sheets

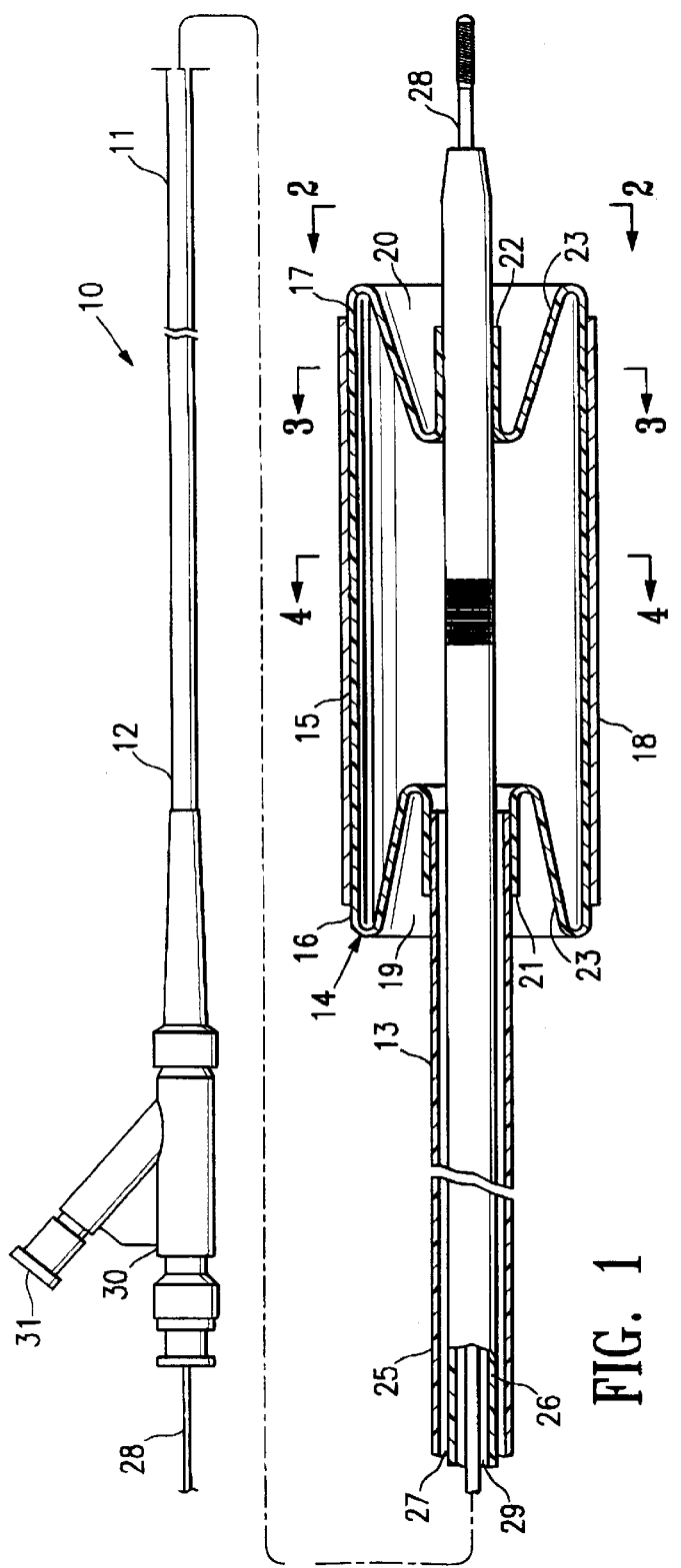
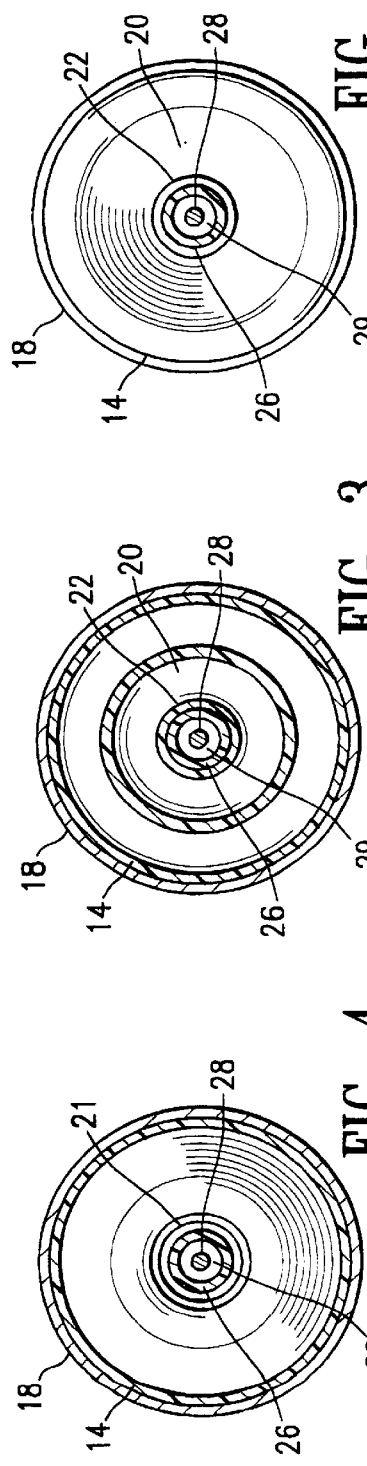
FIG. 1
FIG. 2
FIG. 3
FIG. 4

BALLOON WITH THE VARIABLE RADIAL FORCE DISTRIBUTION

BACKGROUND OF THE INVENTION

This invention generally relates to the filed of intravascular balloon catheters, and more particularly to a balloon catheter with a balloon having a variable radial force along the longitudinal axis for improved expansion and stenting.

Percutaneous transluminal coronary angioplasty (PTCA) is a widely used procedure for the treatment of coronary heart disease. In this procedure, a balloon dilatation catheter is advanced into the patient's coronary artery. The balloon on the catheter is inflated within the stenotic region of the patient's artery, exerting radial force on the stenotic region, to open up the arterial passageway. Thereby increasing the blood flow.

To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced until the preshaped distal tip of the guiding catheter is disposed within the aorta adjacent the ostium of the desired coronary artery, and the distal tip of the guiding catheter is then maneuvered into the ostium. A balloon dilatation catheter may then be advanced through the guiding catheter into the patient's coronary artery until the balloon on the catheter is disposed within the stenotic region of the patient's artery. The balloon is inflated, exerting radial force on the stenotic region, opening up the arterial passageway and increasing the blood flow through the artery.

Generally, the inflated diameter of the balloon is approximately the same diameter as the native diameter of the body lumen being dilated so as to complete the dilatation but not over expand the artery wall. After the balloon is finally deflated, blood flow resumes through the dilated artery and the dilatation catheter can be removed therefrom. However, damage to the vessel wall at and around the stenosis can result from the expansion of the balloon against the vessel wall.

In such angioplasty procedures, there may be a restenosis, i.e. reformation of the arterial blockage. To reduce the restenosis rate and to strengthen the dilated area, physicians frequently implant an intravascular prosthesis, called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. Thereafter, the balloon is deflated to remove the catheter and the stent is left in place within the artery at the site of the dilated lesion.

Stents have been used to open a stenosed vessel for some time. Unfortunately, the force needed to move against the thick stenosis causes the balloon to expand against the vessel wall in the area proximal and distal to the stenosis. The expansion of a stent against the vessel wall can cause damage to the vessel wall, similar to the damage caused by expansion of the balloon.

Therefore, what has been needed is a balloon catheter with improved expansion characteristics to avoid damage to the vessel wall. The present invention satisfies these and other needs.

SUMMARY OF THE INVENTION

The invention is directed to a balloon catheter having an elongated shaft and a balloon mounted on a distal portion of the shaft. The balloon has a working section and proximal and distal end portions that extend inwardly with respect to the working section. The proximal and distal end portions are secured to the catheter shaft within the working section. The balloon catheter of the present invention allows for variable radial force along the catheter's longitudinal axis without changing the outer diameter of the working section of the balloon or the wall thickness throughout the balloon.

The catheter shaft has a proximal end, a distal end, and at least one lumen extending therethrough. The balloon may be configured for dilatation, or for stent delivery with a stent disposed about and mounted on the working section of the balloon. The stent may be any of several known in the art. Such suitable stents include, for example, those described in U.S. Pat. No. 5,507,768 (Lau et al.) and U.S. Pat. No. 5,458,615 (Klemm et al.), which are incorporated herein by reference.

The location of the secured ends of the balloon creates a variable radial force along the balloon working section. Certain areas exert more force, and therefore expand more, against the vessel wall. This phenomenon is called focal expansion. The balloon of the invention has proximal and distal end portions that extend inwardly, creating funnel shaped inverted recesses on each end of the balloon. Generally, balloons known in the art have cone shape end portions extending away from the working section. The inverted recesses create two surface areas inside the balloon at the same location along the longitudinal axis of the catheter shaft between the location that the end is secured to the catheter shaft and the location corresponding to the end of the working length. When the balloon is inflated, the two surface areas exert force in generally opposite directions. The working section of the balloon will exert force against the stenosis. The end portions exert force in a direction determined by design characteristics. In all design embodiments, the force exerted by the end portions will be in a direction generally opposite the force exerted on the stenosis by the working section.

The portions of the working section which have a corresponding surface at the same location along the longitudinal axis of the catheter shaft will not exert the force against the vessel wall that the portion of the working section without a corresponding interior surface will exert. Thereby, the balloon avoids damage to the vessel by limiting expansion of the balloon or stent proximal and distal to the stenosis. Generally, about 40% to about 80% of the length of the working section will have a corresponding surface at the same location along the longitudinal axis of the catheter shaft.

In a specific embodiment, the balloon is at least partially supported by interior fibers of connecting material. The connecting fibers may be made from any material that is compatible with the balloon materials and is noncompliant and rigid in order not to distort beyond its length. These materials include, but are not limited to, polymeric materials and metallic materials. Specifically, biocompatible plastics are adequate materials. The fibers connect at least a portion of the working section with the interior area of the proximal end portion or distal end portion. These fibers allow for a controlled variable radial force. With no fibers, the opposing forces create a lever effect, with most of the force exerted on the end portions cumulatively exerted on the point connecting the end portion to the working length. While this results in less force on the vessel wall at the proximal and distal ends of the working section, it can not be controlled or predicted. With connecting fibers, each connected point along the end portion has a corresponding point on the working section. This in turn allows for a point by point force subtraction, and a controlled and predictable decrease in force along the working section towards the ends.

In one embodiment of the invention, the balloon has a proximal end portion having a tapered length that tapers distally from a larger transverse dimension to a smaller transverse dimension. The tapered length may take any form. Some tapers include, but are not limited to, an embodiment with a tapered length adjacent to the working section with an angle between the working section and the tapered length of about 5 degrees to about 90 degrees. Specifically, the angle is about 30 degrees to about 50 degrees. Another taper embodiment has the tapered length adjacent to the working section and the taper has a radius of curvature. In a third taper embodiment, the tapered length is adjacent to the catheter shaft and includes a portion adjacent to the working section that is generally parallel to the working section. The angle between the tapered length and the catheter shaft is about 5 degrees to about 90 degrees. Specifically, the angle is about 30 degrees to about 50 degrees.

Another embodiment of the balloon has a distal section end portion having a tapered length that tapers proximally from a larger transverse dimension to a smaller transverse dimension. All the embodiments of the tapered length discussed above are also available for the tapered length on the distal end portion. In yet another embodiment of the invention, the balloon has both a proximal end portion and a distal end portion, each with an embodiment of a tapered length.

The balloon is manufactured like many balloons in the art. A balloon may be manufactured with a blow mold manufacturing process. A tube of the balloon material is placed into a mold having an interior with the desired balloon shape. The material is then expanded under certain pressure and temperature to meet the mold interior, which forms the balloon. This balloon is unique in its assembly. The balloon is sealed to the catheter shaft using techniques known in the art, however, the ends must be sealed to allow for proper placement of the ends within the working section. Specifically, the ends are glue sealed at the proper location so that the sealed ends will be within the working section. This may be accomplished by sealing the ends one at a time, or by gathering the balloon between the ends so the balloon working section does not overlap the ends during the sealing process. After the seal is complete, the balloon working section may then be arranged over the sealed ends, and prepared for entry.

In the embodiment having connecting fibers, the balloon assembly is more complex. First, the proximal and distal end portions are secured to the catheter shaft using conventional techniques leaving a free end on each. The connecting fibers are then connected to the end portions at predetermined spaces, leaving free ends. The free ends of the end portions and the connecting fibers are then secured to the working section. Additional methods known in the art may also be considered to place the connecting fibers within the balloon.

The balloon is preferably formed of a semi or low compliant material, such as polyamides including nylon and PEBAX, and polyurethane. The term "compliant" as used herein refers to thermosetting and thermoplastic polymers that exhibit substantial radial growth upon the application of radially expansive force. The radial growth of a balloon formed of a noncompliant material such as PET is typically less than about 0.02 mm/ATM, compared to about 0.025 to about 0.045 mm/ATM for a balloon formed of low compliant material such as nylon 12. However, this balloon may be made of a variety of materials to suit the compliance needs of the procedure.

The balloon catheter of this invention provides for improved focal expansion and stenting due to the variable radial force along the longitudinal axis. Consequently, the balloon catheter avoids damage to vessel walls during expansion of the balloon or stent thereon, and provides excellent control over stent expansion for improved stent implantation. In the embodiment having reinforcing webbing, the radial expansion on the ends of the working section is limited by the opposing forces as well as the length of the webbing. These and other advantages of the invention will become more apparent from the following detailed description of the invention and the accompanying exemplary drawings.

BRIEF DESCRIPTION OF THE DRAWINGS

FIG. 1 is an elevational view, partially in section, of a balloon catheter system that embodies features of the invention, showing the balloon and stent in a partially expanded state.

FIG. 2 is a transverse cross sectional view of the catheter system of FIG. 1 taken along lines 2—2.

FIG. 3 is a transverse cross sectional view of the catheter system of FIG. 1 taken along lines 3—3.

FIG. 4 is a transverse cross sectional view of the catheter system of FIG. 1 taken along lines 4—4.

DETAILED DESCRIPTION OF THE INVENTION

Figure 6:
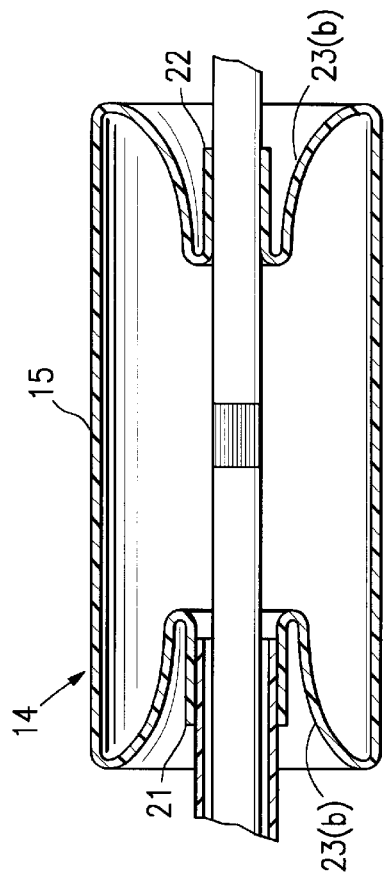
FIG. 6 is an elevational view, partially in section, of the distal section of an alternative embodiment that has a curved taper.

FIGS. 1–4 illustrate a balloon catheter 10 embodying features of the invention, which generally include an elongated catheter shaft 11 having a proximal section 12 and a distal section 13 and a balloon 14 on the distal section 13. In the embodiment shown in FIG. 1, an adapter 30 is on the proximal section 12 of the catheter shaft 11. Balloon 14 has a working section 15. A stent 18 is disposed about the balloon 14 to form a stent deploying catheter system.

FIG. 1 shows an embodiment characterized by a guidewire 28 disposed within the guidewire lumen 29 defined by inner tubular member 26. The catheter shaft 11 has an outer tubular member 25 and an inner tubular member 26. Outer tubular member 25, together with inner tubular member 26, defines an inflation lumen 27 in fluid communication with the balloon 14 and the inflation port 31 on the adapter 30. Inflation fluid may be introduced into the inflation port 31, through the inflation lumen 27, and subsequently inflate the balloon 14.

In FIG. 1, the working section 15 has a proximal end 16 and a distal end 17. The balloon 14 is secured to the catheter shaft 11 at a proximal secured end 21 and a distal secured end 22. The balloon 14 is sealingly secured to the catheter shaft 11 within the working section 15. The balloon 14 may be secured to the catheter shaft 11 on either or both the inner or outer wall of the balloon 14. The balloon 14 has a proximal end portion 19, and a distal end portion 20. The proximal end portion 19 and the distal end portion 20 extend inwardly with respect to the working section 15.

A feature of the embodiment shown in FIG. 1 is the tapered length 23. A tapered length may exist between the working section distal end 17 and the distal secured end 22, and another tapered length may exist between the working section proximal end 16 and the proximal secured end 21. FIG. 1 embodies one configuration of the tapered length 23. In the end portions 19 and 20 illustrated in FIG. 1, the end portions 19 and 20 comprise funnel shaped inverted recesses with an inner diameter which is defined by an outer surface of the balloon which decreases from a location adjacent to the working section ends 16 and 17 to an end of the secured ends 21 and 22.

Figure 5:
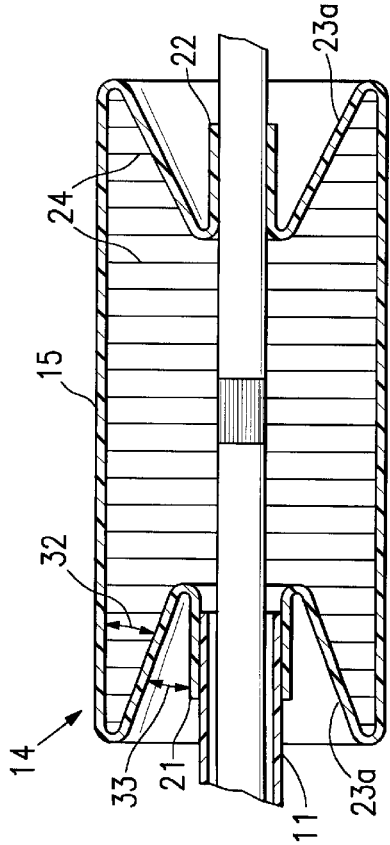
FIG. 5 is an elevational view, partially in section, of the distal section of an alternative embodiment that has connecting fibers connecting the working length to the tapering portions.

FIG. 5 shows a similar configuration of the tapered length 23(a). In this configuration, the tapered length is adjacent to the working section 15, and extends generally to the secured ends 21 and 22. The angle 32 between the balloon working section 15 and the tapered length 23(a) is generally about 5 degrees to about 90 degrees. In the embodiment illustrated, the angle 32 is about 30 to about 50 degrees. The angle 33 between the tapered length 23(a) and the catheter shaft 11 is generally about 5 degrees to about 90 degrees. In the embodiment illustrated, the angle 33 is about 30 to about 50 degrees.

Figure 7:
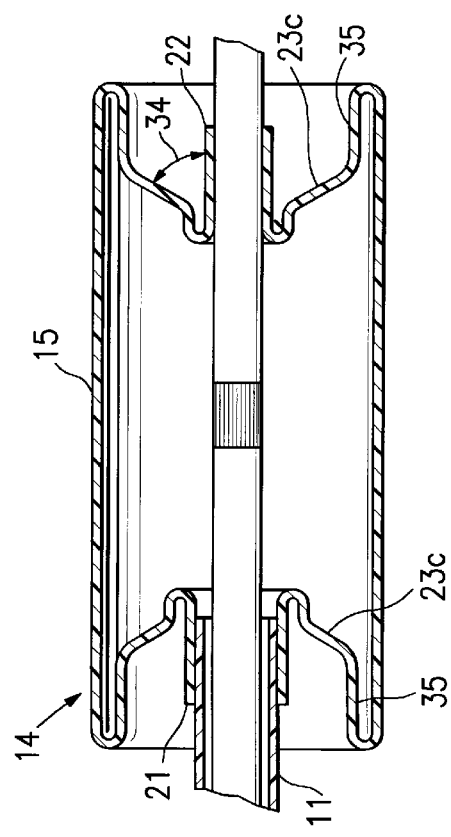
FIG. 7 is an elevational view, partially in section, of the distal section of an alternative embodiment that has a tapered portion and including a portion generally parallel to the working length.

FIG. 6 shows another configuration of the tapered length feature 23(b). The tapered length 23(b) may exist adjacent to the working section 15 with a radius of curvature and extending generally to the secured ends 21 and 22. A third configuration is shown in FIG. 7 with tapered length 23(c). The tapered length 23(c) is adjacent to the secured ends 21 and 22 with an angle 34 between the tapered length 23(c) and the catheter shaft 11 of about 5 degrees to about 90 degrees. In the embodiment illustrated, the angle 34 is about 34 to about 60 degrees. A portion 35 between the working section 15 and the tapered length 23(c) extends generally parallel to the working section 15.

Referring back to FIG. 5, an embodiment of the invention includes connecting fibers 24 connecting at least a portion of the inner surface of the working section 15 and the inner surface of the tapered length 23(a). The connecting fibers 24 may also extend between the inner surface of the working section 15 and the outer surface of the catheter shaft 11. Preferably, the connecting fibers 24 are generally perpendicular to the longitudinal axis of the balloon working section 15. The connecting fibers 24 may be made of either polymeric material or metallic material. Specifically, the connecting fiber material may be made of biocompatible plastic.

The balloon 14 is assembled in such a way as to allow the proximal secured end 21 and the distal secured end 22 to be within the working section 15. This may be accomplished by securing proximal secured end 21, then moving balloon 14 and securing distal secured end 22. Then the balloon 14 will be arranged around the secured ends 21 and 22. Other methods may also be used to secure the secured ends 21 and 22 within the working section 15.

Figure 8:
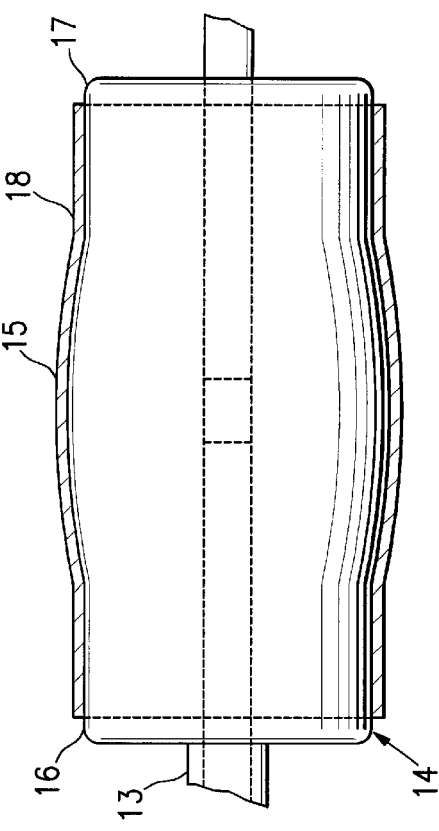
FIG. 8 is an elevational view, partially in section, of the distal section of the catheter system of the invention as shown in FIG. 1 depicting the balloon and stent fully expanded.

FIG. 8 shows the distal section 13 of the catheter shaft 11 of the embodiment illustrated in FIG. 1. The embodiment shown in FIG. 8 shows the balloon 14 inflated with the stent 18 expanded for deployment. FIG. 8 further illustrates an advantage of this embodiment, which shows that the working section 15 expands to a larger radius at its center than the radius of expansion at the working section proximal end 16 or the working section distal end 17 at the working pressure.

Although individual features of embodiments of the invention may be shown in some of the drawings and not in others, those skilled in the art will recognize that individual features of the embodiments of the invention can be combined with any or all the features of another embodiment.

What is claimed is:

1. A balloon catheter, comprising
   a) a catheter shaft having a proximal end, a distal end, and at least one lumen; and
   b) a balloon on a distal section of the catheter shaft, the balloon having an inflated configuration, and having a central working section with a proximal end and a distal end, and having proximal and distal end portions which extend inwardly with respect to the working section, and having a proximal secured section and a distal secured section secured to the catheter shaft and located at positions on the shaft which are between the proximal end and the distal end of the working section of the balloon in the inflated configuration, the proximal secured section having a proximal end located distal to the proximal end of the working section.

2. The balloon catheter of claim 1 wherein the end portions comprise funnel shaped inverted recesses with an inner diameter which is defined by an outer surface of the balloon which decreases from a location adjacent to the working section end to an end of the secured end.

3. The balloon catheter of claim 1, wherein the proximal end portion has a tapered length tapering distally from a larger transverse dimension to a smaller transverse dimension.

4. The balloon catheter of claim 1, wherein the working section has a proximal working section radially aligned with the proximal end portion of the balloon and a distal working section radially aligned with the distal end portion of the balloon, and the proximal and distal working sections have lengths which are about 40% to about 80% of the total working section length.

5. The balloon catheter of claim 3, wherein the tapered length is adjacent to the working section, and the tapered length extends to the catheter shaft.

6. The balloon catheter of claim 5 wherein an angle between the working section and the tapered length is about 30 degrees to about 50 degrees, and an angle between the tapered length and the catheter shaft is about 30 degrees to about 50 degrees.

7. The balloon catheter of claim 3, wherein the tapered length is adjacent to the catheter shaft and including a portion between the working section and the tapered length which extends generally parallel to the working section.

8. The balloon catheter of claim 7, wherein the angle between the catheter shaft and the tapered length is about 30 degrees to about 60 degrees.

9. The balloon catheter of claim 3, wherein the tapered length is adjacent to the working section, and the tapered length has a radius of curvature.

10. The balloon catheter of claim 1, further comprising a connecting fiber connecting at least a portion of the working section to the proximal and distal end portions.

11. The balloon catheter of claim 10, wherein the connecting fiber is selected from the group consisting of polymeric materials and metallic materials.

12. The balloon catheter of claim 10, further comprising a connecting fiber connecting at least a portion of the working section to the catheter shaft.

13. The balloon catheter of claim 1, wherein the distal end portion has a tapered length tapering proximally from a larger transverse dimension to a smaller transverse dimension.

14. The balloon catheter of claim 13, wherein the tapered length is adjacent to the working section, and the tapered length extends to the catheter shaft.

15. The balloon catheter of claim 14, wherein an angle between the working section and the tapered length is about 30 degrees to about 50 degrees, and an angle between the tapered length and the catheter shaft is about 30 degrees to about 50 degrees.

16. The balloon catheter of claim 13, wherein the tapered length is adjacent to the catheter shaft and including a portion between the working section and the tapered length which extends generally parallel to the working section.

17. The balloon catheter of claim 16, wherein the angle between the catheter shaft and the tapered length is about 30 degrees to about 60 degrees.

18. The balloon catheter of claim 13, wherein the tapered length is adjacent to the working section, the tapered length has a radius of curvature, and the tapered length extends to the catheter shaft.

19. The balloon of claim 1 wherein the distal secured section has a distal end located proximal to the distal end of the working section.

20. A balloon catheter, comprising
a) a catheter shaft having a proximal end, a distal end, and at least one lumen; and
b) a balloon on the distal end of the catheter shaft, the balloon having an inflated configuration, and having a central working section with a proximal end and a distal end, and having a proximal secured section and a distal secured section secured to the catheter shaft and located at positions on the shaft which are between the proximal end and the distal end of the working section of the balloon in the inflated configuration, the proximal secured section having a proximal end located distal to the proximal end of the working section.

21. A balloon catheter assembly, comprising
a) a catheter shaft having a proximal end, a distal end, and at least one lumen;
b) a balloon on the distal end of the catheter shaft, the balloon having an inflated configuration, and having a central working section with a proximal end and a distal end, and having a proximal secured section and a distal secured section secured to the catheter shaft and located at positions on the shaft which are between the proximal end and the distal end of the working section of the balloon in the inflated configuration, the proximal secured section having a proximal end located distal to the proximal end of the working section; and
c) a stent disposed about the balloon.

22. A balloon catheter, comprising
a) a catheter shaft having a proximal end, a distal end, and at least one lumen; and
b) a balloon on a distal section of the catheter shaft, the balloon having an inflated configuration, and having a central working section with a proximal end and a distal end, and having proximal and distal end portions which extend inwardly with respect to the working section, and having a proximal secured section and a distal secured section secured to the catheter shaft, the majority of the proximal secured section being located between the proximal end and the distal end of the working section of the balloon in the inflated configuration.

23. A balloon catheter, comprising
a) a catheter shaft having a proximal end, a distal end, and at least one lumen; and
b) a balloon on a distal section of the catheter shaft, the balloon having an inflated configuration, and having a central working section with a proximal end and a distal end, and having proximal and distal end portions which extend inwardly with respect to the working section, and having a proximal secured section and a distal secured section secured to the catheter shaft, the working section has a proximal working section radially aligned with the proximal end portion of the balloon and a distal working section radially aligned with the distal end portion of the balloon and the length of the proximal and distal working sections are about 40% to about 80% of the total working section length.

* * * * *

UNITED STATES PATENT AND TRADEMARK OFFICE
CERTIFICATE OF CORRECTION

PATENT NO.   : 6,391,002 B1
DATED        : May 21, 2002
INVENTOR(S)  : Arkady Kokish It is certified that error appears in the above-identified patent and that said Letters Patent is hereby corrected as shown below:

<u>Column 5,</u>
Line 47, change "34 to about 60 degrees", to read -- 30 to about 60 degrees --.

Signed and Sealed this

Twenty-second Day of October, 2002

*Attest:*

*Attesting Officer*

JAMES E. ROGAN
*Director of the United States Patent and Trademark Office*